United States Patent
Bohnen et al.

(12)

(10) Patent No.: US 6,437,187 B1
(45) Date of Patent: Aug. 20, 2002

(54) COMPOUNDS HAVING AN IONIC STRUCTURE USED AS CONSTITUENT OF AN OLEFIN POLYMERISATION CATALYST

(75) Inventors: Hans Bohnen, Moers; Cornelia Fritze, Frankfurt; Frank Kueber, Oberursel, all of (DE)

(73) Assignee: Targor GmbH, Mainz (DE)

( * ) Notice: Subject to any disclaimer, the term of this patent is extended or adjusted under 35 U.S.C. 154(b) by 0 days.

(21) Appl. No.: 09/622,418

(22) PCT Filed: Feb. 13, 1999

(86) PCT No.: PCT/EP99/00957

§ 371 (c)(1), (2), (4) Date: Aug. 16, 2000

(87) PCT Pub. No.: WO99/43685

PCT Pub. Date: Sep. 2, 1999

(30) Foreign Application Priority Data

Feb. 27, 1998 (DE) .......................................... 198 08 254

(51) Int. Cl.[7] .............................. C07F 9/02; C07F 5/02; B01J 31/00; C08F 4/64
(52) U.S. Cl. .......................... 568/9; 502/103; 502/117; 526/134; 526/160; 526/190; 526/943; 556/403; 556/404; 568/6; 568/12; 568/16; 568/17
(58) Field of Search ................. 568/6, 12, 16, 568/17, 9; 556/403, 404; 502/103, 117; 526/134, 160, 193, 943

(56) References Cited

U.S. PATENT DOCUMENTS 4,224,256 A 9/1980 Klemann et al. .............. 568/6
4,898,802 A 2/1990 Hsieh et al. ................. 430/110
5,348,299 A 9/1994 Clapper Jr. .................. 273/138

FOREIGN PATENT DOCUMENTS

| EP | 520 732 | 12/1992 |
|---|---|---|
| EP | 558 158 | 9/1993 |
| EP | 427 697 | 5/1996 |
| WO | WO 95/24268 | 9/1995 |

OTHER PUBLICATIONS

Angew.Chem.1995,107,1255–1283, Britzinger et al.
Adv.Org.Chem., vol. 18, 99–149, Sinn et al.
J.Am.Chem.Soc., 1991,113,3623–3625, Yang et al.
J.Org.Chem., 71(1974)C21–C24, Eisch et al.
Chem Abst.XP–002105323.
J.Am.Chem.Soc., 1975, 97(4), 895–7.
Chem.Abstr XP 002105325, 1972.*
Ann. Chem. 1967, 705, 66–75, Hellwinkel et al.*
Chem.Ber., 1966 99(11) 3660–7, Hellwinkel.*
Chem.Ber., 1996 99(11), 3642–59, Hellwinkel.*
Chem.Abstr. XP 002105326, 1972.*
Chem.Abstr. XP 002105327, 1972.*
Chem.Ber., Bd.97, 1964,S.747–768,Wittig et al.*
Chem. Abstract vol. 77 No. 4 (1972) –XP–002105324.

\* cited by examiner

*Primary Examiner*—Porfirio Nazario-Gonzalez
(74) *Attorney, Agent, or Firm*—Keil & Weinkauf

(57) ABSTRACT

Novel chemical compounds have an ionic structure and in combination with an organometallic transition metal compound form a catalyst system which is advantageously used for the polymerization of olefins.

11 Claims, No Drawings

COMPOUNDS HAVING AN IONIC STRUCTURE USED AS CONSTITUENT OF AN OLEFIN POLYMERISATION CATALYST

The present invention relates to chemical compounds which have an ionic structure and in combination with an organometallic transition metal compound form a catalyst system which can advantageously be used for the polymerization of olefins.

Ziegler-type catalysts based on angled metallocenes of metals of group IV form a new generation of industrially usable catalysts for the polymerization of α-olefins (H. H. Brintzinger, D. Fischer, R. Mülhaupt, R. Rieger, R. Waymouth, Angew. Chem. 1995, 107,1255–1283).

To obtain an active catalyst system, the metallocene complex is treated with a large excess of methylaluminoxane (MAO) (H. Sinn, W. Kaminsky, Adv. Organomet. Chem., 1980, 18, 99). Apart from the high cocatalyst costs, this has the disadvantage of a high aluminum content in the polymer obtained. For this reason, new activation methods which make do without superstoichiometric amounts of activator have been developed.

The synthesis of "cation-like" metallocene polymerization catalysts is described in J. Am. Chem. Soc. 1991, 113, 3623. Here, the alkyl group is abstracted from an alkyl-metallocene compound by means of trispentafluorophenylborane which is used in a stoichiometric amount relative to the metallocene.

EP-A-0,427,697 claims this synthetic principle and a corresponding catalyst system comprising an uncharged metallocene species (e.g. $Cp_2ZrMe_2$), a Lewis acid (e.g. $B(C_6F_5)_3$) and aluminum alkyls. A process for preparing salts of the formula $LMX^+XA^-$ according to the above-described principle is claimed in EP-A-0,520,732.

EP-A-0,558,158 describes zwitterionic catalyst systems which are prepared from dialkyl-metallocene compounds and salts of the formula $[R_3NH]^+[BPh_4]^-$. The reaction of such a salt with, for example, $Cp_2*ZrMe_2$ results in protolysis with elimination of methane to give a methyl-zirconocene cation as an intermediate. This reacts via C—H activation to give the zwitterion $Cp_2*Zr^+$-(m-$C_6H_4$)-$BPh_3^-$. Here, the Zr atom is covalently bound to a carbon atom of the phenyl ring and is stablilized by means of an agostic hydrogen bond.

U.S. Pat. No. 5,348,299 claims corresponding systems in which dimethylanilinium salts with perfluorinated tetraphenylborates are used. Apart from the activating action of the borate salts, their ligand sphere excercises an important influence on the reaction equilibrium. Large bulky ligands largely prevent the dimerization of the metallocenium fragments and thus displace the equilibrium to the side of the catalytically active species. The previously described mononuclear borate anions have four aryl ligands and can, as a result of the incorporation of bulky groups on the ligand, exercise an influence on the reaction equilibrium (WO 95/24268). Disadvantages of these systems are the complicated syntheses, and also the extreme sensitivity of the resulting metallocenium complexes.

It is an object of the present invention to provide a chemical compound having a novel ligand system which retains the advantages of bulky ligands but does not have the disadvanatages of the existing bulky aryl ligands.

We have found that this object is achieved by a chemical compound of the formula I, $$[M^1Q_x^1Q_y^2Q_z^3]^\ominus A^\beta \quad (I)$$

where
  $M^1$ is an element of group IIa, IIa, IVa or Va of the Periodic Table of the Elements,
  x is 0 or 1,
  y is 0 or 1 and
  z is 0 or 1 and
  A is a cation of group Ia, IIa, IIIa of the Periodic Table of the Elements, a carbenium, oxonium, phosphonium or sulfonium cation or a quaternary ammonium compound, and
  Q is a ligand system based on a biphenyl skeleton which is bound to $M^1$ via the positions 2 and 12 and has the formula (II)

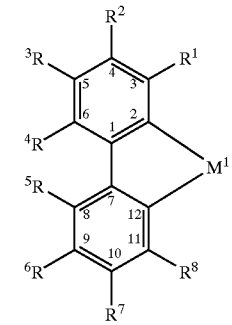

where
  $R^1$, $R^2$, $R^3$, $R^4$, $R^5$, $R^6$, $R^7$ and $R^8$ are identical or different and are each a hydrogen atom, a halogen atom, a $C_1$–$C_{40}$ group such as $C_1$–$C_{20}$-alkyl, $C_1$–$C_{20}$-haloalkyl, $C_1$–$C_{10}$-alkoxy, $C_6$–$C_{40}$-aryl, $C_6$–$C_{40}$-haloaryl, $C_6$–$C_{40}$-aryloxy, $C_7$–$C_{40}$-arylalkyl, $C_7$–$C_{40}$-haloarylalkyl or $C_7$–$C_{40}$-haloalkylaryl, or an $OSiR_3^9$ group, where $R^9$ are identical or different and are each a hydrogen atom, a halogen atom or a $C_1$–$C_{40}$ group such as $C_1$–$C_{20}$-alkyl, $C_1$–$C_{20}$-haloalkyl, $C_1$–$C_{10}$-alkoxy, $C_6$–$C_{40}$-aryl, $C_6$–$C_{40}$-haloaryl, $C_6$–$C_{40}$-aryloxy, $C_7$–$C_{40}$-arylalkyl, $C_7$–$C_{40}$-haloarylalkyl or $C_7$–$C_{40}$-haloalkylaryl. Furthermore, two or more radicals $R^1$ to $R^8$ may be connected to one another in such a way that they form a monocyclic or polycyclic ring system which may in turn be substituted.

Preference is given to compounds in which $M^1$ is boron and which have the formula (III), $$[BQ^1Q^2]^\ominus A^\oplus \quad (III)$$

where
  A is a cation of group la, lha, Ilia of the Periodic Table of the Elements, a carbenium, oxonium, phosphonium or sulfonium cation or a quaternary ammonium compound,
  $Q^1$ and $Q^2$ may be identical or different and are each a ligand system based on a biphenyl skeleton which is bound to B via the positions 2 and 12, where Q corresponds to the groups indicated under the formula (II).

Preference is likewise given to compounds in which $M^1$ is phosphorus and which have the formula (IV), $$[PQ^1Q^2Q^3]^\ominus A^\oplus \quad (IV)$$

where

A is a cation of group Ia, IIa, IIIa of the Periodic Table of the Elements, a carbenium, oxonium, phosphonium or sulfonium cation or a quaternary ammonium compound, $Q^1$, $Q^2$, $Q3$ are identical or different and are each a ligand system based on a biphenyl skeleton which is bound to P via the positions 2 and 12, where Q is as defined for the formula (II).

Particularly preferred but nonlimiting examples of the novel chemical compound of the formulae (III) or (IV) are:

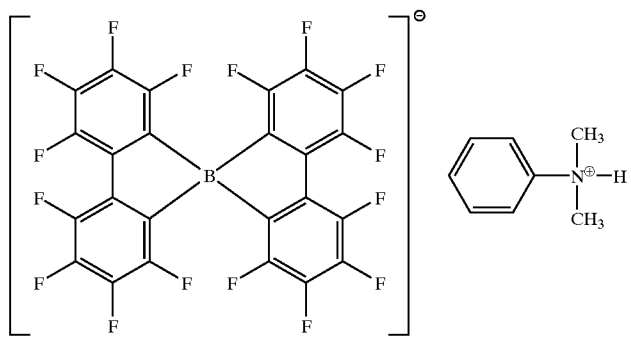

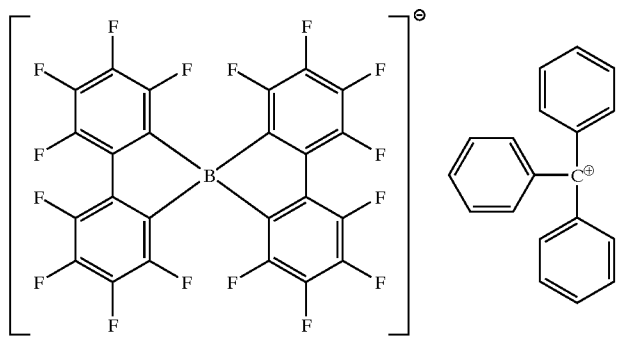

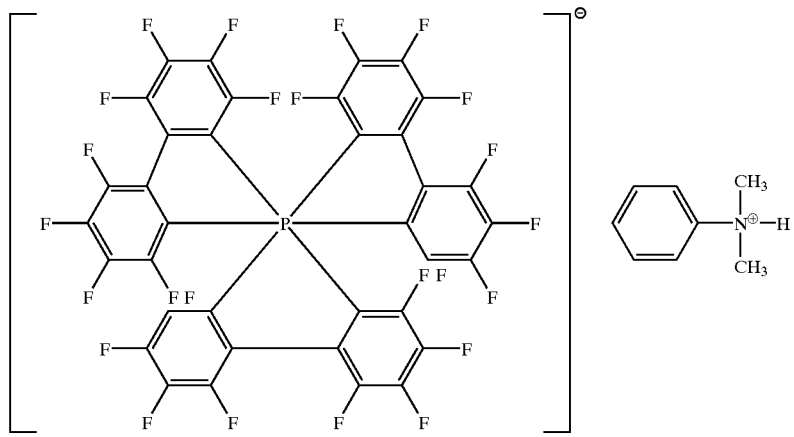

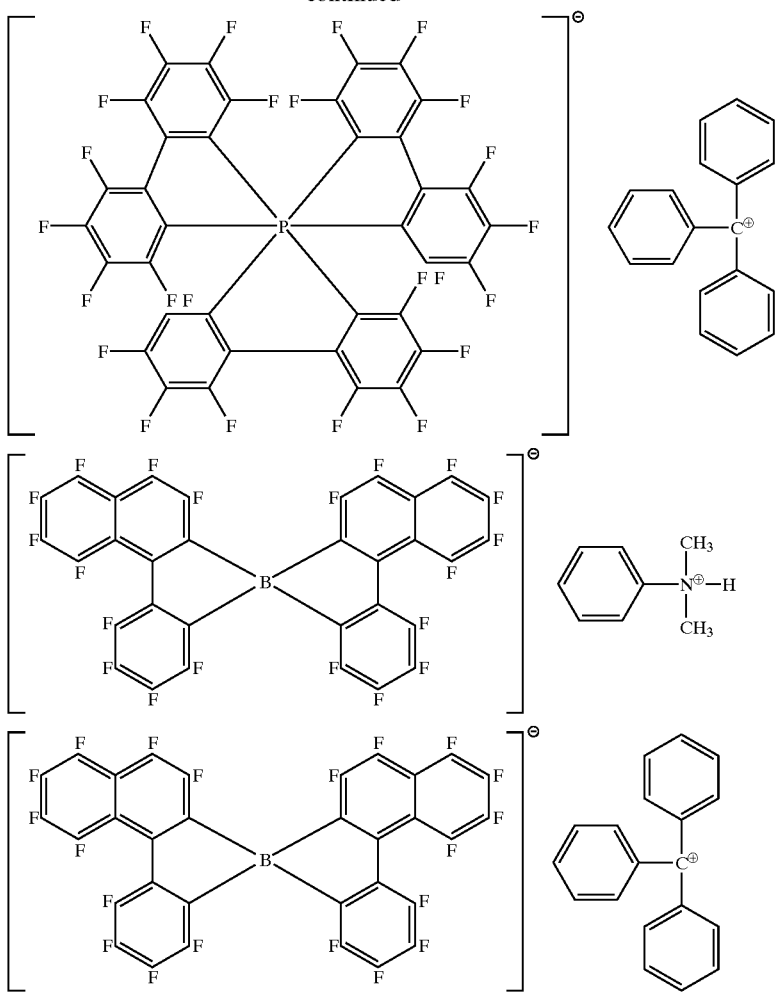
A novel chemical compound of the formula (I) can be prepared, for example, according to the following reaction scheme:
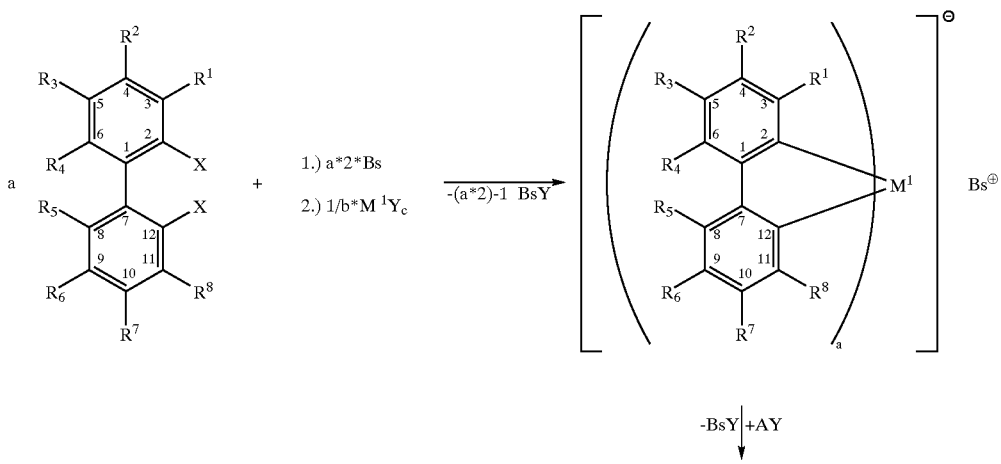

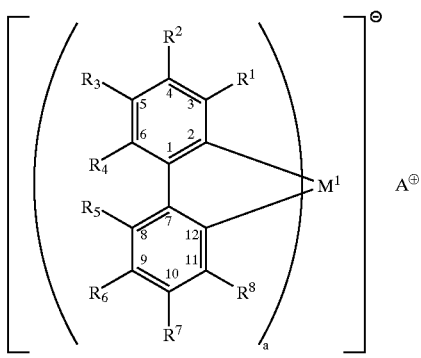

where
- Bs is a base, preferably an element of group Ia or IIa of the Periodic Table of the Elements or an organolithium compound or a Grignard compound,
- X independently of one another are identical or different and are each a leaving group, preferably a hydrogen or halogen atom,
- Y independently of one another are identical or different and are each a leaving group, preferably a hydrogen or halogen atom,
- $M^1$ is an element of group IIa, IIIa, IVa or Va of the Periodic Table of the Elements,
- A is a cation of group Ia, IIa, IIa of the Periodic Table of the Elements, a carbenium, oxonium or suffonium cation or a quaternary ammonium compound,
- a is 2 or 3,
- b is an integer from 2 to 5 and
- c is an integer from 2 to 5.

The compounds of the present invention can be used together with metallocenes as catalyst systems in the polymerization of olefins, in particular the preparation of homopolymers or copolymers based on ethylene, propylene or norbornadiene, and also of functionalized olefins.

The following examples illustrate the invention.

EXAMPLE 1

Synthesis of 2,2'-dibromooctafluorobiphenyl 10 g of 1,2-dibromotetrafluorbenzene (32 mmol) together with 100 ml of diethyl ether are placed in a reaction vessel and cooled to −78° C. 15 ml of n-butyllithium (2.5 M in hexane) are added dropwise and the mixture is stirred for 1 hour. An excess of titanium tetrachloride is subsequently added and the mixture is stirred for another 4 hours at −78° C. The suspension is allowed to warm to room temperature and is stirred for another 10 hours. It is then hydrolyzed using $H_2O$. The aqueous phase is shaken a number of times with diethyl ether and the organic phases are subsequently combined and dried over magnesium sulfate. The solvent is taken off and the residue is recrystallized from a 1:1 mixture of diethyl ether/n-pentane.

$^{19}$F-NMR $CDCl_3$: −127.5 ppm (m, 2F, 3,3'-F), −134.6 ppm (m, 2F, 6,6'-F), −149.9 ppm (m, 2F, 4,4'-F), −154.3 ppm (m, 2F, 5,5'-F)

EXAMPLE 2

Synthesis of N,N-dimethylanilinium bis(2,2'-octafluorobiphenyl)borate 4.6 g (10 mmol) of 2,2'-dibromooctafluorobiphenyl together with 30 ml of diethyl ether are placed in a reaction vessel and stirred at −78° C. 8 ml of n-butyllithium (2M in hexane) are subsequently added dropwise and the suspension is stirred for 2 hours at −78° C. 5 ml of boron trichloride (1 M in hexane) are then added dropwise and the suspension is warmed to room temperature. The solvent is taken off under reduced pressure and the residue is stirred with 100 ml of pentane. Subsequently, 0.79 g of N,N dimethylanilinium chloride is added a little at a time and the mixture is stirred for another 5 hours. The solid obtained is filtered off and extracted with 50 ml of methylene chloride. The filtrate obtained is evaporated under reduced pressure and the resulting solid is recrystallized from a methylene chloride/pentane mixture (1:1).

$^{19}$F-NMR $CDCl_3$: −137.2 ppm (m, 2F, 3,3'-F), −138.4 ppm (m, 2F, 6,6'-F), −159.9 ppm (m, 2F, 4,4'-F), −160.9 ppm (m, 2F, 5,5'-F)

EXAMPLE 3

Synthesis of triphenylcarbenium bis(2,2'-ocatfluorobiphenyl)borate 4.6 g (10 mmol) of 2,2'-dibromooctafluorobiphenyl together with 30 ml of diethyl ether are placed in a reaction vessel and stirred at −78° C. 8 ml of n-butyllithium (2M in hexane) are subsequently added dropwise and the suspension is stirred for 2 hours at −78° C. 5 ml of boron trichloride (1 M in hexane) are then added dropwise and the suspension is warmed to room temperature. The solvent is taken off under reduced pressure and the residue is stirred with 100 ml of pentane. 1.39 g of triphenylchloromethane are subsequently added a little at a time and the mixture is stirred for another 10 hours. The solid obtained is filtered off and extracted with 70 ml of methylene chloride. The filtrate obtained is evaporated under reduced pressure and the resulting solid is recrystallized from a methylene chloride/pentane mixture (1:1).

$^{19}$F-NMR $CDCl_3$: −137.4 ppm (m, 2F, 3,3'-F), −138.8 ppm (m, 2F, 6,6'-F), −160.4 ppm (m, 2F, 4,4'-F), −161.3 ppm (m, 2F, 5,5'-F)

EXAMPLE 4

Synthesis of triphenylcarbenium tris(2,2'-octafluorobiphenyl)phosphate 5.93 g (12 mmol) of 2,2'-dibromooctafluorobiphenyl together with 30 ml of diethyl ether are placed in a reaction vessel and stirred at −78° C. 9.6 ml of n-butyllithium (2.5 M in hexane) are subsequently added dropwise and the suspension is stirred for 2 hours at −78° C. 0.83 g of PCl$_5$ dissolved in 10 ml of Et$_2$O is then added dropwise and the suspension is warmed to room temperature. The solvent is taken off under reduced pressure and the residue is stirred with 100 ml of pentane. 1.10 g of triphenylchloromethane are subsequently added a little at a time and the mixture is stirred for another 10 hours. The solid obtained is filtered off and extracted with 70 ml of methylene chloride. The filtrate obtained is evaporated under reduced pressure and the resulting solid is recrystallized from a methylene chloride/pentane mixture (1:1).

$^{19}$F-NMR CDCl$_3$: −133.9 ppm (m, 2F, 3,3'-F), −134.4 ppm (m, 2F, 6,6'-F), −157.4 ppm (m, 2F, 4,4'-F), −158.5 ppm (m, 2F, 5,5'-F)

EXAMPLE 5

Synthesis of N,N-dimethylanilinium tris(2,2'-octafluorobiphenyl)phosphate 5.93 g (12 mmol) of 2,2'-dibromooctafluorobiphenyl together with 30 ml of diethyl ether are placed in a reaction vessel and stirred at −78° C. 9.6 ml of n-butyllithium (2.5 M in hexane) are subsequently added dropwise and the suspension is stirred for 2 hours at −78° C. 0.83 g of PCl$_5$ dissolved in 10 ml of Et$_2$O is then added dropwise and the suspension is warmed to room temperature. The solvent is taken off under reduced pressure and the residue is stirred with 100 ml of pentane. 0.63 g of N,N-dimethylanilinium chloride is subsequently added a little at a time and the mixture is stirred for another 5 hours. The solid obtained is filtered off and extracted with 70 ml of methylene chloride. The filtrate obtained is evaporated under reduced pressure and the resulting solid is recrystallized from a methylene chloride/pentane mixture (1:1).

$^{19}$F-NMR CDCl$_3$: −133.1 ppm (m, 2F, 3,3'-F), −133.6 ppm (m, 2F, 6,6'-F), −157.0 ppm (m, 2F, 4,4'-F), −158.1 ppm (m, 2F, 5,5'-F)

We claim:
1. A compound of the formula I,

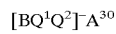   (I)

where

A is a cation of group Ia, IIa, IIIa of the Periodic Table of the Elements, a carbenium, oxonium, phosphonium or sulfonium cation or a quaternary ammonium compound, Q is a ligand system based on a biphenyl skeleton which is bound to B via the positions 2 and 12 and has the formula (II)

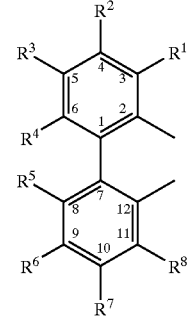

where

R$^1$, R$^2$, R$^3$, R$^4$, R$^5$, R$^6$, R$^7$ and R$^8$ are identical or different and are each a halogen atom, a C$_1$–C$_{40}$ group or an OSiR$_3$9 group, where R$^9$ are identical or different and are each a hydrogen atom, a halogen atom or a C$_1$–C$_{40}$ group.

2. A compound of the formula III,

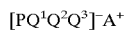   (III)

where

A is a cation of group Ia, IIa, IIIa of the Periodic Table of the Elements, a carbenium, oxonium, phosphonium or sulfonium cation or a quaternary-ammonium compound, Q is a ligand system based on a biphenyl skeleton which is bound to P via the positions 2 and 12 and has the formula (II)

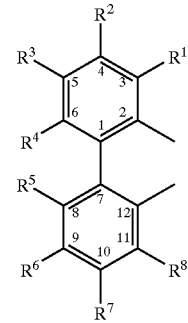

where

R$^1$, R$^2$, R$^3$, R$^4$, R$^5$, R$^6$, R$^7$ and R$^8$ are identical or different and are each a halogen atom, a C$_1$–C$_{40}$ group or an OSiR$_3$9 group, where R$^9$ are identical or different and are each a hydrogen atom, a halogen atom or a C$_1$–C$_{40}$ group.

3. A compound as claimed in claim 2, wherein, in the formula (II), two or more radicals R$^1$ to R$^8$ are connected to one another in such a way that they form a monocyclic or polycyclic ring system which may in turn be substituted.

4. A catalyst for polymerizing olefins comprising
(1) an organometallic transition metal compound and
(2) A compound

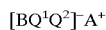   (I)

as defined in claim 1 or

UNITED STATES PATENT AND TRADEMARK OFFICE
CERTIFICATE OF CORRECTION

PATENT NO.    : 6,437,187 B1
DATED         : August 20, 2002
INVENTOR(S)   : Bohnen et al.

It is certified that error appears in the above-identified patent and that said Letters Patent is hereby corrected as shown below:

<u>Column 8,</u>
Line 66, the formula "$[BQ^1Q^2]\ A^{30}$" should be -- "$[BQ^1Q^2]\ A^+$ --.

Signed and Sealed this

Fifteenth Day of October, 2002

*Attest:*

JAMES E. ROGAN
*Attesting Officer*      *Director of the United States Patent and Trademark Office*